US011008598B2

(12) United States Patent
Foody et al.

(10) Patent No.: US 11,008,598 B2
(45) Date of Patent: May 18, 2021

(54) PROCESS COMPRISING ACID PRETREATMENT AND ENZYMATIC HYDROLYSIS

(71) Applicant: Iogen Corporation, Ottawa (CA)

(72) Inventors: Brian Foody, Ottawa (CA); Jeffrey S. Tolan, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 15/550,525

(22) PCT Filed: Mar. 16, 2016

(86) PCT No.: PCT/CA2016/050288
§ 371 (c)(1),
(2) Date: Aug. 11, 2017

(87) PCT Pub. No.: WO2016/145527
PCT Pub. Date: Sep. 22, 2016

(65) Prior Publication Data
US 2018/0037915 A1 Feb. 8, 2018

Related U.S. Application Data

(60) Provisional application No. 62/269,311, filed on Dec. 18, 2015, provisional application No. 62/142,068, filed on Apr. 2, 2015, provisional application No. 62/133,609, filed on Mar. 16, 2015.

(51) Int. Cl.
| | | |
|---|---|---|
| *C12P 19/02* | (2006.01) | |
| *C12P 19/14* | (2006.01) | |
| *C12P 7/02* | (2006.01) | |
| *C12P 7/10* | (2006.01) | |
| *D21C 1/00* | (2006.01) | |
| *D21C 1/04* | (2006.01) | |
| *D21C 5/00* | (2006.01) | |

(52) U.S. Cl.
CPC ............... *C12P 19/02* (2013.01); *C12P 7/02* (2013.01); *C12P 7/10* (2013.01); *C12P 19/14* (2013.01); *D21C 1/00* (2013.01); *D21C 1/04* (2013.01); *D21C 5/005* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 2,418,167 A | 4/1947 | Du Bois | |
| 5,424,417 A | 6/1995 | Torget et al. | |
| 5,789,210 A | 8/1998 | Ho et al. | |
| 5,866,382 A | 2/1999 | Hallborn et al. | |
| 6,475,768 B1 | 11/2002 | Otero et al. | |
| 6,582,944 B1 | 6/2003 | Hallborn et al. | |
| 7,348,168 B2 | 3/2008 | Wu et al. | |
| 7,375,197 B2 | 5/2008 | Adney et al. | |
| 7,527,927 B1 | 5/2009 | Ho et al. | |
| 7,527,951 B2 | 5/2009 | Londesborough et al. | |
| 7,585,652 B2 | 9/2009 | Foody et al. | |
| 7,622,284 B2 | 11/2009 | Op Den Camp et al. | |
| 7,754,456 B2 | 7/2010 | Penttila et al. | |
| 8,038,842 B2 | 10/2011 | Retsina et al. | |
| 8,101,398 B2 | 1/2012 | St-Pierre et al. | |
| 8,268,125 B2 | 9/2012 | Retsina et al. | |
| 8,409,836 B2 | 4/2013 | Vehmaanpera et al. | |
| 8,435,771 B2 | 5/2013 | Ren et al. | |
| 8,703,453 B2 | 4/2014 | Larsen | |
| 8,709,770 B2 | 4/2014 | Harlick et al. | |
| 8,728,243 B2 | 4/2014 | van der Meulen et al. | |
| 8,815,499 B2 | 8/2014 | Alriksson et al. | |
| 8,815,561 B2 | 8/2014 | Liu et al. | |
| 8,834,633 B2 | 9/2014 | van der Meulen et al. | |
| 8,871,475 B2 | 10/2014 | Alriksson et al. | |
| 9,012,188 B2 | 4/2015 | Van Heiningen | |

(Continued)

FOREIGN PATENT DOCUMENTS

| | | |
|---|---|---|
| WO | 1991/05039 A1 | 4/1991 |
| WO | 2006/034590 A1 | 4/2006 |

(Continued)

OTHER PUBLICATIONS

Zhu et al. "Sulfite pretreatment (SPORL) for robust enzymatic saccharification of spruce and red pine." Bioresource Technology 100.8 (2009): 2411-2418. (Year: 2009).*
Sassner et al., "Steam Pretreatment of Salix with and without SO2 Impregnation for Production of Bioethanol," 2005, Applied Biochemistry and Biotechnology, pp. 1101-1117, vol. 121-124.
International Preliminary Report on Patentability dated Sep. 19, 2017 for PCT Application No. PCT/CA2016/050288, filed Mar. 16, 2016.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.

(Continued)

*Primary Examiner* — Emily A Cordas
(74) *Attorney, Agent, or Firm* — Knobbe, Martens, Olson & Bear, LLP (57) ABSTRACT

Provided herein is a process for producing a fermentation product from a lignocellulosic feedstock. The process comprises soaking a lignocellulosic feedstock in an aqueous solution to produce a soaked feedstock. The soaked feedstock is at least partially dewatered and the at least partially dewatered feedstock is subjected to pretreating. The pretreatment chemical is sulfur dioxide, sulfurous acid or a combination thereof and can be added to the process at any stage prior to and/or during pretreatment. The pretreated feedstock composition is fed to an enzymatic hydrolysis conducted at a temperature that is higher than 58° C. The cellulose in the pretreated feedstock composition is hydrolyzed with cellulase enzymes in the presence of the dissolved solids to produce glucose. The glucose is fermented to produce the fermentation product.

35 Claims, 1 Drawing Sheet

(56) References Cited

U.S. PATENT DOCUMENTS

| | | |
|---|---|---|
| 9,090,915 B2 | 7/2015 | Wang et al. |
| 9,102,951 B2 | 8/2015 | Griffin et al. |
| 9,290,821 B2 | 3/2016 | Blackbourn et al. |
| 9,574,212 B2 | 2/2017 | Foody et al. |
| 2006/0068475 A1 | 3/2006 | Foody |
| 2007/0254348 A1 | 11/2007 | Retsina et al. |
| 2009/0118477 A1 | 5/2009 | Hallberg et al. |
| 2010/0056774 A1 | 3/2010 | Anand et al. |
| 2010/0279361 A1 | 11/2010 | South et al. |
| 2011/0165643 A1 | 7/2011 | Restina et al. |
| 2011/0300586 A1 | 12/2011 | Liu et al. |
| 2012/0041186 A1 | 2/2012 | Pschorn et al. |
| 2012/0052534 A1* | 3/2012 | Harlick ............ C12P 7/10 435/105 |
| 2012/0073199 A1 | 3/2012 | Lewis |
| 2012/0237983 A1* | 9/2012 | Harlick ............ C12P 19/14 435/99 |
| 2013/0071903 A1 | 3/2013 | Rowland et al. |
| 2014/0034047 A1 | 2/2014 | Retsina et al. |
| 2014/0053827 A1 | 2/2014 | Baudel et al. |
| 2014/0142351 A1 | 5/2014 | Johnston et al. |
| 2014/0154746 A1 | 6/2014 | Jonsson et al. |
| 2014/0163210 A1 | 6/2014 | Retsina et al. |
| 2014/0178944 A1 | 6/2014 | Parekh et al. |
| 2014/0182582 A1 | 7/2014 | Retsina et al. |
| 2014/0186899 A1 | 7/2014 | Retsina et al. |
| 2014/0186903 A1 | 7/2014 | Retsina et al. |
| 2015/0259709 A1 | 9/2015 | Retsina et al. |
| 2016/0257979 A1 | 9/2016 | Restina et al. |

FOREIGN PATENT DOCUMENTS

| | | | |
|---|---|---|---|
| WO | 2006/034591 A1 | 4/2006 | |
| WO | 2006/128304 A1 | 12/2006 | |
| WO | 2008/025164 A1 | 3/2008 | |
| WO | 2008/041840 A1 | 3/2010 | |
| WO | 2010022511 A1 | 3/2010 | |
| WO | WO-2010022511 A1 * | 3/2010 | ............ C08H 8/00 |
| WO | 2013/113579 A1 | 8/2013 | |
| WO | 2014/106222 A2 | 7/2014 | |
| WO | 2015/004098 A1 | 1/2015 | |
| WO | 2016/145528 A1 | 9/2016 | |
| WO | 2016/145529 A1 | 9/2016 | |
| WO | 2016/145530 A1 | 9/2016 | |
| WO | 2016/145531 A1 | 9/2016 | |

OTHER PUBLICATIONS

Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.

Shuai et al., "Cornparitive study of SPORL and dilute-acid pretreatments of spruce for cellulosic ethanol production," 2010, Bioresource Technology, pp. 3106-3114, vol. 2010.

Sipos et al., "Steam pretreatment of dry and ensiled industrial hemp for ethanol production," 2010, Biomass and Bioenergy, pp. 1-11.

Soderstrom et al. "Effect of Washing on Yield in One- and Two-Step Steam Pretreatment of Softwood for Production of Ethanol," 2004, Biotehncol, Prog., pp. 744-749, vol. 20.

Soderstrom et al., "Separate versus Simultaneous Saccharification and Fermentation of Two-Step Steam Pretreated Softwood for Ethanol Production," 2005, Journal of Wood Chemistry, pp, 187-202, vol. 25.

Soderstrom et al. "Two-Step Steam Pretreatment of Softwood with SO2 impregnation for Ethanol Production," 2002, Applied Biochemistry and Biotechnology, pp. 5-21, vol. 98-100.

Szengyel et al., "Cellulase Production of Trichoderma reesei Rut C 30 Using Steam-Penetrated Spruce," 2000, Applied Biochemistry and Biotechnology, pp. 679-691, vol. 84-86.

Tengborg et al., "Comparison of SO2 and H2504 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain Saccharomyces cerevisiae without detoxification," 2010, Bioresource Technology, pp. 8678-8685, vol. 101.

Trajano et al. "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergetic effects of mixing hybrid poplar and wheat straw biomass for bioconversion processes," 2015, Biotechnol Biofuels, pp. 1-10, vol. 8:226.

Von Sivers et al., "A Techno-Economical Comparison of Three Processes for the Production of Ethanol from Pine," 1995, Bioresource Technology, pp. 43-52, vol. 51.

Wang et al., "Lignosulfonate and elevated pH can enhance enzymatic saccharification of lignocelluloses," 2013, Biotechnology for Biofuels, pp, 1-10, vol. 6:9.

Wang et al., "Ethanol production from poplar wood through enzymatic saccharification and fermentation by dilute acid and SPORL pretreatrnents," 2012, Fuel, pp. 606-614, vol. 95.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp, 208-215, vol. 126.

Wolfinger et al., "Modeling of the Acid Sulfite Pulping Process.—Problem Definition and Theoretical Approach for a solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology, 11052-11062, vol. 102.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

Fan et al., "Optimization of SO2-catalyzed hydrolysis of corncob for xylose and xylitol production," 2014, J Chem Technol Biotechnol, pp. 1720-1726, vol. 89.

Zhang et al., "Sulfite (SPORL) pretreatment of switchgrass for enzymatic saccharification," 2013, Bioresource Technology, pp, 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhu et al., "Woody biomass pretreatment for cellulosic ethanol production: Technology and energy consumption evaluation," 2010, Bioresource Technology, pp. 4992-5002, vol. 101.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Ethanol production from SPORL-pretreated lodgepole pine: preliminary evaluation of mass balance and process energy efficiency," 2010, App Microbiol Biotechnol, pp, 1355-1365, vol. 86.

(56) References Cited

OTHER PUBLICATIONS

Zhu et al., "High Titer Ethanol Production from Forest Residue Using Sulfite Mill Pulping Chemistry," 2015, Presentation at 2015 TAPPI IBBC.
Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.
Zhu et al., "On Polydispersity of Plant Biomass Recalcitrance and its Effects on Pretreatment Optimization for Sugar Production," 2011, Bioenerg, Res., pp. 201-210, vol. 4.
Zhu et al., Quantitative predictions of bioconversion of aspen by dilute acid and SPORL pretreatments using a unified combined hydrolysis factor (CHF), 2012, Process Biochemistry, pp. 785-791, vol. 47.
Zhu et al., "Sulfite pretreatment (SPORL) for robust enzymatic saccharification of spruce and red pine," 2009, Bioresource Technology, pp. 2411-2418, vol. 100.
Barber et al., "Antimicrobial intermediates of the general phenylpropanoid and lignin specific pathways," 2000, Phytochemistry, pp. 53-56, vol. 54.
Berka et al., "Comparative genomic analysis of the thermophilic biomass-degrading fungi Myceliophthora thermophila and Thielavia terrestris", 2011; Nature Biotechnology, p. 922, vol. 29.
Dong et al., "Antimicrobial and antioxidant activities of lignin from residue of corn stover to ethanol production", 2011, Industrial Crops and Products, pp. 1629-1634, vol. 34.
Dotsenko et al., "Cloning, purification, and characterization of Galactomannan-degrading enzymes from Myceliophthora therrnophila," 2012, Biochemistry, pp. 1303-1311, vol. 77.
Gilbert et al., "Characterization of the enzymes present in the cellulose system of Thielavia terrestris 255B," 1992, Bioresource Technology, pp. 147-154, vol. 39.
Sujak et al., "Thermostability of proteins: role of metal binding and pH on the stability of the dinuclear CuA site of Thermus thermophilus," 2007, Biophysical Journal, pp. 2645-2651, vol. 93.
Zemek et al., "Antibiotic properties of lignin components", 1979, Folia Microbiol., pp. 483-486, vol. 24.
Cavka et al., "Identification of small aliphatic aldehydes in pretreated lignocellulosic feedstocks and evaluation of their inhibitory effects on yeast", 2015, J. Agric. Food Chem., 63, 9747-9754.
Tao et al., "Process and technoeconomic analysis of leading pretreatment technologies for lignocellulosic ethanol production using switchgrass," 2011, Bioresource Technology, 102, pp. 11105-11115.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 21/21.
Sendelius et al., "Steam Pretreatment Optimisation for Sugarcane Bagasse in Bioethanol Production," 2005, Master of Science Thesis, Lund University, Sweden.
Bensah, E. and Mensah, M., "Chemical Pretreatment Methods for the Production of Cellulosic Ethanol: Technologies and Innovations," International Journal of Chemical Engineering, 2013, pp. 1-21, vol. 2013.
Bhalla, A. et al., "Improved lignocellulose conversion to biofuels with thermophilic bacteria and thermostable enzymes," Bioresource Technology, 2013, pp. 751-759, vol. 128.
Boussaid, A., et al., "Fermentability of the Hemicellulose-Derived Sugars from Stearn-Exploded Softwood (Douglas Fir).", Biotechnology and Bioengineering, 1999, pp. 284-289, vol. 64, No. 3.
Brownell, H. and Saddler, J., "Steam Pretreatment of Lignocellulosic Material for Enhanced Enzymatic Hydrolysis," Biotechnology and Bioengineering, 1987, pp. 228-235, vol. 29.
Bura, et al., "Moving towards commercialization of lignocellulosic biomass to fuels to chemicals. How to deal with heterogeneous biomass?" University of Washington Biofuels and Bioproducts Laboratory, 2012.
Bura, R., et al,, "Influence of Xylan on the Enzymatic Hydrolysis of Steam-Pretreated Corn Stover and Hybrid Poplar," Biotechnol Prog, 2009, pp. 315-322, vol. 25, No. 2.
Bura, R., et al., "SO2-Catalyzed Steam Explosion of Corn Fiber for Ethanol Production", Applied Biochemistry and Biotechnology, 2002, pp. 59-72, vols. 98-100.
Carrasco, C., et al., "SO2-catalysed steam pretreatment of quinoa stalks," J Chem Technol Biotechnol, 2015, pp. 64-71; vol. 90.
Carrasco, C., et al., "SO2-catalyzed steam pretreatment and fermentation of enzymatically hydrolyzed sugarcane bagasse," Enzyme and Microbial Technology, 2010, pp. 64-73, vol. 46.
Carrasco, C., "Arabinosylated phenolics obtained from SO2-steam-pretreated sugarcane bagasse," Journal of Chemical Technology and Biotechnology, 2012, pp. 1723-1726, vol. 87.
Chacha, N., et al., "Steam Pretreatment of Pine (Pinus patula) Wood Residue for the Production of Reducing Sugars," Cellulose Chemistry and Technology, 2011, pp. 495-501, vol. 45 (7-8).
Chandra, R., et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark, T.A. et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark, T.A. et al., "Steam Explosion of the Softwood Pinus Radiata with Sulphur Dioxide Addition. I. Process Optimization," Journal of Wood Chemistry and Technology, 1967, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chern. Res, 2007, pp. 7711-7720, vol. 46.
Dekker, R.F.H. et ai., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F, H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.
Ehsanipour, Mandana "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995. Bioresource Engineering, pp. 225-229, vol. 52.
Elander, et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.

(56) References Cited

OTHER PUBLICATIONS

Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol, Prog., pp. 807-819, vol. 25, No. 3.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Monavari et al., "Improved One-Step Steam Pretreatment if SO2-Impregnated Softwood with Time-Dependant Temperature Profile for Ethanol Production," 2010, Biotechnol, Prog., pp. 1054-1060, vol. 26, No. 4.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry arid Biotechnology, 561-576, vol. 84-86.
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 19-145, vol. 44.
Ramos et al. "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 621-831, vol. 15.
Kumar et al., Effects of Cellulase and Xylanase Enzymes on the Deconstruction of Solids from Pretreatment of Poplar by LeadingTechnologies, Biotechnol. Prag., vol. 25, No. 2, (2009) pp. 302-314.
Felby et al., "Ethanol from Wheat Straw Cellulose by Wet Oxidation Pretreatment and Simultaneous Saccharifcation and Fermentation," American Chemical Society, ACS Symposium Series, 2003, pp. 157-174.

\* cited by examiner

PROCESS COMPRISING ACID PRETREATMENT AND ENZYMATIC HYDROLYSIS

CROSS-REFERENCE TO RELATED APPLICATIONS

This application is a national stage application of PCT/CA2016/050288 having an international filing date of Mar. 16, 2016, which claims the priority benefit of provisional application No. 62/133,609, filed Mar. 16, 2015, provisional application No. 62/142,068, filed Apr. 2, 2015, and provisional application No. 62/269,311, filed Dec. 18, 2015, all of which are incorporated herein by reference.

TECHNICAL FIELD

The present disclosure relates to a process for producing one or more products from a lignocellulosic feedstock by a process comprising pretreatment and cellulose hydrolysis.

BACKGROUND

The production of fuel ethanol, or other fuels and chemicals, from lignocellulosic feedstocks provides an attractive alternative to the feedstocks predominantly used to date such as corn starch, sugar cane, and sugar beets. The production of fermentation products from these latter sources cannot increase much further as most of the farmland suitable for the production of these crops is in use. Cellulose is an abundant natural polymer, so there is an enormous untapped potential for its use as a source for fuels and chemicals. Also, lignocellulosic feedstocks to be used for fuel or chemical production are inexpensive as they have limited use. Another advantage of using these feedstocks for fuel or chemical production is that lignin, which is a byproduct of the cellulose conversion process, can be used as a fuel to power the conversion process, thereby avoiding the use of fossil fuels. Several studies have concluded that, when the entire production and consumption cycle is taken into account, the use of ethanol produced from cellulose generates close to nil greenhouse gases.

The conversion of lignocellulosic feedstocks to a fermentation product may be carried out with a pretreatment process prior to subsequent biological treatment(s). The pretreatment may, but does not always, include the addition of a chemical such as an acid or alkali. In any case, the primary goal of pretreatment may be to make the feedstock more amenable to subsequent enzymatic hydrolysis with cellulase enzymes to liberate glucose. The pH of the pretreated feedstock composition resulting from the pretreatment is adjusted to a pH that is suitable for the cellulase enzymes used to produce glucose, unless the pH of the pretreated feedstock composition is already in the suitable range. The cellulase enzymes then convert the cellulose to glucose and the glucose can then be converted to a fermentation product including ethanol or other fuels or chemicals by yeast or bacterium using known methods. However, one challenge with known methods for producing glucose from lignocellulosic feedstocks is that the enzyme requirement may be high, which may add cost and/or affect commercialization.

Pretreatment of lignocellulosic feedstocks with dilute sulfuric acid at elevated temperature is described in the literature. Such a pretreatment produces an aqueous pretreated feedstock composition in which a large amount of soluble degradation products are present including phenolic lignin and furfural. These compounds are often perceived as problematic in that they inhibit and/or inactivate the cellulase enzymes and thus are often diluted by adding water or removed by washing the aqueous pretreated feedstock composition with water prior to carrying out enzymatic hydrolysis. Alternatively, the compounds are removed by treating the liquor by precipitation with lime or other alkali at pH above 8, or by microfiltration methods such as nanofiltration. Unfortunately, there is significant capital and operating cost associated with these processes.

Another chemical pretreatment that has received attention is pretreatment with sulfur dioxide. Sulfur dioxide is a gas that may be dissolved in water to provide a sulfurous acid solution. Sulfur dioxide and/or sulfurous acid may be added to the lignocellulosic feedstock upstream to and/or in a pretreatment reactor by any of a number of methods, including adding sulfur dioxide gas to the lignocellulosic feedstock or combining dilute sulfurous acid with the lignocellulosic feedstock. Sulfur dioxide and/or sulfurous acid has been reported for use in pretreating dry, presteamed, or prewetted feedstocks such as wood chips. As with sulfuric acid, sulfur dioxide and/or sulfurous acid pretreatment produces soluble compounds that are potentially inhibitory and/or inactivating to cellulase enzymes. These compounds are often diluted with water to decrease their concentration or removed by washing with water prior to hydrolysis. The compounds can alternatively be removed by treating the liquor with precipitation using alkali such as lime or by a microfiltration technique, as described previously in connection with sulfuric acid pretreatment. Similar to sulfuric acid pretreatment, there is significant capital and operating cost associated with these processes.

Another problem often associated with the fermentation of sugar to ethanol or other fermentation products is that the hydrolysis and/or fermentation may be prone to microbial contamination. Microbes can be introduced into the process at any stage, for instance during enzymatic hydrolysis, but may be particularly problematic during fermentation. For example, microbes that originate in the hydrolysis can carry forward to the fermentation process and outcompete the yeast. In fact, during fermentation, bacteria can propagate quickly as the optimum conditions of the fermentation are also conducive to their growth. Unwanted byproducts that can be produced by bacterial contaminants during fermentation include lactic acid, acetone and propionic acid. Lactic acid is a common byproduct produced by bacteria such as *Lactobacillus* spp, *Pediococcus* spp, *Leuconostoc* spp and/or *Weissella* spp (among others) during ethanol fermentations. The production of such undesirable byproducts decreases the yield of the desired fermentation product as the bacteria compete with the yeast for fermentable sugars and convert them to undesirable byproducts instead of the fermentation product of interest. Moreover, organic acids and other byproducts can be inhibitory to the yeast. Each of these factors can contribute to decreases in the efficiency of the fermentation by lengthening the time required for carrying out the fermentation, increasing the amount of yeast required and/or decreasing the final yields of the desired fermentation product from the fermentable sugars. Microbial contamination can also lead to plant shutdown to sterilize equipment, which may translate to a significant reduction in revenue from a plant.

Unwanted microbes during fermentation may be controlled by introducing antibiotics, oxidizing agents or other anti-microbial chemicals to the fermentation. For example, de Oliva-Neto and Yokoya (Brazilian Journal of Microbiology, 2001, 3:10-14) examined the effect of a variety of antimicrobial compounds on the viability of *Saccharomyces cerevisiae, Lactobacillus* and *Leuconostoc* in fermentations carried out on cane juice to produce ethanol. This included formulated chemicals, such as zinc manganese ethylenebis (dithiocarbamate), methyldithiocarbamate, 3-methyl-4-chlorophenol, 2-benzyl-4-chlorophenol and o-phenylphenol, 2-chloroacetamide and others, that are commonly recommended for use in microbial control in sugar and alcohol production plants. Antibiotics tested included penicillum, clindamycin and cephamandole. The results showed that current chemical biocides used in industrial fuel alcoholic fermentations reduced yeast viability, while antibiotics were effective at reducing bacterial growth, without affecting yeast viability. However, the use of antibiotics in fuel ethanol applications has its limitations as microbial contaminants are known to develop antibiotic resistance (Lushia and Heist, 2005, Ethanol Producer Magazine, Antibiotic-Resistant Bacteria in Fuel Ethanol Fermentations).

Bacterial control in industrial fuel alcoholic fermentation can also be carried out by sulfuric acid washing of yeast cell suspensions. The goal of the acid treatment is to destroy contaminating microorganisms that cannot withstand low pH conditions, without a substantial reduction in yeast viability or fermentative capacity of the fermentation. However, achieving this balance may be difficult to achieve in practice.

SUMMARY

Disclosed herein is a process for producing a fermentation product from a lignocellulosic feedstock that includes a sulfurous acid and/or sulfur dioxide pretreatment. Although sulfur dioxide and/or sulfurous acid based pretreatments may produce potentially inhibitory and/or inactivating products, it has been found that the degree of inactivation and/or inhibition of these products is lower than those obtained from sulfuric acid pretreatment. Moreover, it has been found that a reduction in enzyme usage is possible. Remarkably, this reduction in enzyme usage relative to a comparable process including a sulfuric acid pretreatment is even more evident for unwashed systems (i.e., where the pretreated material is not washed or is minimally washed before hydrolysis). Since unwashed systems are advantageous in terms of simplicity, reduced water usage, and reduced loss of pentose sugars produced during pretreatment, the advantages of this combination are significant. In particular, cost savings related to reduced enzyme usage and/or reduced water usage may be sizable.

In addition, when sulfur dioxide/sulfurous acid pretreatment is followed by a hydrolysis conducted at a temperature above about 58° C., with little or no washing of the pretreated material, there may be even more advantages. For example, one factor to consider during enzymatic hydrolysis, particularly if the consistency of the pretreated material is relatively high (e.g., above 10 wt %) is that considerable energy may be required for actively mixing the slurry throughout the hydrolysis. In addition to increasing energy usage, this relatively high energy may, at least in part, contribute to a slow temperature rise of the slurry that is often observed as the hydrolysis progresses. In practice, this increase in temperature is often addressed by using cooling water in a jacket to cool the slurry down to the optimum temperature of the enzyme (e.g., about 50° C. for conventional cellulase). By conducting the hydrolysis at a temperature above 58° C., less cooling water needs to be added to address the slow temperature rise, since it is not likely that the temperature would increase much above this value. In addition, the higher hydrolysis temperature may reduce the viscosity of the slurry, and thus may reduce the amount of energy required for mixing. Furthermore, conducting the hydrolysis at a temperature above about 58° C., may provide an economical approach to reducing contamination by unwanted microbes. Accordingly, the sugar and/or alcohol yield are not as likely to be lowered by microbial contamination. This additional protection against microbial contamination may be particularly advantageous for sulfur dioxide and/or sulfurous acid catalyzed pretreatments, wherein less potent inhibitors are formed. In fact, even though pretreatment with sulfur dioxide and/or sulfurous acid may produce fewer, different, and/or less potent inhibitors than pretreatment with sulfuric acid, it is still surprising that providing little or no washing before hydrolysis does not significantly affect sugar yield.

In accordance with one embodiment, there is provided a process for producing one or more products from a lignocellulosic feedstock, wherein the process includes a pretreatment comprising the addition of sulfur dioxide and/or sulfurous acid to the lignocellulosic feedstock, in which low concentrations of inhibitors, such as furfural and/or hydroxyl-methylfurfural (HMF), are generated. Advantageously, the enzymatic hydrolysis is conducted at a temperature that is higher than conventional, and in particular, higher than the optimum growth temperature and/or maximum growth temperature of common contaminating microbes, thus reducing the risk of microbial contamination (e.g., which may result due to fewer or reduced levels of inhibitors). On the other hand, since the potency of inhibitory compounds is relatively low during hydrolysis, the enzymatic hydrolysis may proceed with improved efficiency relative to other processes in which more potent inhibitory compounds are produced.

Advantageously, by pretreating the lignocellulosic feedstock with sulfur dioxide and/or sulfurous acid, and conducting the enzymatic hydrolysis at a temperature selected to limit bacterial growth and/or destroy the microbes, it may be possible that fermentation can proceed more efficiently, without compromising the performance of the enzymes. For example, many microbes may be relatively inactive at temperatures above about 58° C. and/or destroyed at temperatures above about 62.5° C. While high temperature may potentially reduce enzyme performance due to its destabilizing impact on the enzyme, the presence of less potent inhibitors released during pretreatment may off-set this negative effect. Such increased enzyme performance at high temperature may in turn reduce the amount of enzyme required in the process, while also reducing potential downtime due to microbial contamination. Further improvements in performance, and thus economics, may be achieved if a thermophilic and/or thermostable enzyme is used. For example, further improvements in performance, and thus economics, may be achieved if enzyme having an optimal activity greater than about 58° C. or 60° C. is used.

Thus, according to a first embodiment, there is provided a process for producing a fermentation product from a lignocellulosic feedstock comprising: treating the lignocellulosic feedstock in one or more stages, thereby producing a pretreated feedstock composition comprising at least cellulose, said treating including combining a pretreatment chemical selected from sulfur dioxide, sulfurous acid, or a combination thereof, with the lignocellulosic feedstock; hydrolyzing at least a portion of the cellulose in the pretreated feedstock composition in an enzymatic hydrolysis to produce glucose, and fermenting the glucose with microorganisms to produce the fermentation product, wherein the pretreated feedstock composition comprises dissolved solids that are fed to the enzymatic hydrolysis such that a concentration of the dissolved solids at an inlet to the enzymatic hydrolysis is at least about 30% of a concentration of the dissolved solids in the pretreated feedstock composition, and wherein said hydrolyzing is conducted at a temperature greater than 58° C.

According to second embodiment, there is provided a process for producing an alcohol from a lignocellulosic feedstock comprising: (i) soaking the lignocellulosic feedstock in an aqueous solution to produce a soaked feedstock; (ii) at least partially dewatering the soaked feedstock to produce a feedstock that is at least partially dewatered; (iii) pretreating the partially dewatered feedstock with heat at a temperature in the range of about 170° C. to about 230° C. to produce a pretreated feedstock composition, wherein sulfur dioxide, sulfurous acid, or a combination thereof, are added: (a) to the aqueous solution used in soaking, (b) to the lignocellulosic feedstock prior to soaking, (c) to the lignocellulosic feedstock after the step of soaking and prior to or during pretreating, or (d) a combination thereof; (iv) feeding at least 70% (w/w) of the amount of dissolved solids in the pretreated feedstock composition to an enzymatic hydrolysis, wherein said dissolved solids comprise at least furfural; (v) hydrolyzing the cellulose from the pretreated feedstock composition in the enzymatic hydrolysis to produce glucose, said hydrolyzing conducted with one or more cellulases, wherein the hydrolyzing is conducted at a temperature greater than 58° C. so as to reduce or prevent bacterial contamination, yeast contamination, or a combination thereof, (vi) fermenting the glucose with microorganisms to produce the alcohol; and (vii) recovering the alcohol by distillation or pervaporation.

BRIEF DESCRIPTION OF THE DRAWINGS

Exemplary embodiments will now be described in conjunction with the drawing in which.

DETAILED DESCRIPTION

Feedstock

Embodiments of the process utilize a lignocellulosic feedstock. By the term "lignocellulosic feedstock", it is meant any type of woody or non-woody plant biomass or feedstock derived from plant biomass. The combined content of cellulose, hemicellulose and lignin in the lignocellulosic feedstock is typically greater than 25 wt % (w/w). Sucrose, fructose and starch can be present, but typically in lesser amounts than cellulose and hemicellulose.

Examples of lignocellulosic feedstock are known to those skilled in the art and include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum (including sweet sorghum), cord grass, rye grass, miscanthus, reed canary grass, C3 grasses such as *Arundo donax* or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks. Moreover, new lignocellulosic feedstock varieties may be produced from any of those listed above by plant breeding or by genetic engineering.

In an embodiment, the lignocellulosic feedstock is (i) an energy or biomass crop, (ii) an agricultural residue and/or (iii) hardwood.

In a further embodiment, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In another embodiment, the lignocellulosic feedstock is a non-woody lignocellulosic feedstock such as (i) an energy crop, and/or (ii) an agricultural residue.

In another embodiment of the invention, the lignocellulosic feedstock is straw, stover or an energy crop. As used herein, straw refers to the stem, stalk and/or foliage portion of crops remaining after the removal of starch and/or sugar containing components for consumption. Examples of straw includes, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include but are not limited to soybean stover, sorghum stover and corn stover.

Lignocellulosic feedstocks that have particle sizes of less than about 6 inches may not require size reduction. For feedstocks of larger particle sizes, the feedstock may be subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In one embodiment, at least 90% by volume of the particles produced from the size reduction may have a length less than between about 1/16 and about 6 inches. Suitable equipment for the particle size reduction is a hammer mill, a refiner or a roll press as disclosed in WO 2006/026863.

The feedstock may be slurried in water prior to soaking. The production of an aqueous slurry may allow the feedstock to be pumped.

The lignocellulosic feedstock may also be leached prior to soaking as set forth in WO 02/070753 (Griffin, which is incorporated herein by reference). Removal of sand from the feedstock may also be carried out using wet or dry sand removal techniques that are known in the art. Examples include the use of a hydrocyclone or a sieve.

Soaking

The lignocellulosic feedstock may be soaked in water or an aqueous solution prior to pretreating. The soaking can be conducted at any stage prior to pretreating. For example, the soaking can be conducted before, during or subsequent to a size reduction step. The aqueous solution may include a pretreatment chemical, such as an acid or base. The water or aqueous solution may be provided from a recycle stream obtained from other stages of the process. The soaking is typically conducted in a tank or other suitable equipment to handle soaked material.

Soaking may be carried out in the presence of sulfur dioxide and/or sulfurous acid. Sulfurous acid is the aqueous solution of sulfur dioxide. Soaking may also involve the addition of water. When water only is used for soaking, the sulfur dioxide and/or sulfurous acid can be added to the feedstock downstream of soaking (e.g., prior to or during pretreating). For example, the sulfur dioxide and/or sulfurous acid can be added to a feedstock that has been at least partially dewatered after being soaked.

The soaking is typically conducted at low consistency. Examples of consistency ranges at which the soaking can be conducted include between about 1 wt % and about 20 wt % (wt:wt), or about 2 wt % and about 18 wt %, or between about 3 wt % and about 15 wt % undissolved solids as determined by the method of Example 1. The soaking may be carried out at any suitable temperature and duration. For example, in one embodiment, soaking is carried out at 20° C. to 80° C. for a duration in the range of about 1 minute to about 20 minutes, or longer. Soaking may be carried out in one or more batch or continuous vessels, or a combination thereof. The vessels may be mixed vessels, unmixed vessels, or a combination thereof. In one embodiment, the soaking is part of a leaching process.

Dewatering

The feedstock may be at least partially dewatered to increase the undissolved solids content relative to the incoming feedstock. That is, the feedstock may be dewatered to increase the consistency (e.g., the amount of undissolved dry solids or "UDS" of a sample, which may be expressed as a ratio on a weight basis (wt:wt), or as a percent on a weight basis, for example, % (w/w), also denoted herein as wt %) prior to further processing. For example, in one embodiment, the feedstock is dewatered subsequent to soaking. The term dewatering refers to removing at least a portion of the water or aqueous solution present in the feedstock (e.g., introduced during the soaking step and/or to form a slurry) and may include the removal of water and/or a solution comprising sulfurous acid. The dewatering may involve removing the aqueous solution under pressure from the feedstock, or at atmospheric pressure, as discussed below.

There are a variety of known devices that can be utilized to at least partially dewater the soaked feedstock. Some examples include drainers, filtration devices, screens, plug formation devices, extruders or a combination thereof.

In certain embodiments, a plug formation device may be used to at least partially dewater the soaked feedstock and form a plug of material, although separate devices for dewatering and plug formation can be employed. Without being limiting, a plug formation device suitable for use in the process described herein is a pressurized screw press.

Liquid separated from the lignocellulosic feedstock by the dewatering step may be reused in the process, such as for slurrying and/or soaking the incoming feedstock, as described previously.

Examples of plug formation devices include a pressurized screw press, a co-axial piston screw feeder, a modular screw device or a plug screw feeder.

If the feedstock is subjected to dewatering under pressure, the pressure increase may be caused by one or more high pressure pumps. The pump or other feeding device increases the pressure of the feedstock prior to dewatering to e.g., about 45 psia to about 900 psia, or about 70 psia to about 800 psia or about 140 psia to about 800 psia. The pressure may be measured with a pressure sensor located at a feedstock inlet port on a dewatering device or a plug formation device that also dewaters the feedstock. Alternatively, the feedstock subjected to dewatering may be at atmospheric pressure or at a pressure below about 45 psia.

There may be an optional step of pre-draining the feedstock in order to drain out liquid from a feedstock at atmospheric pressure or higher. This pre-drained feedstock can then be subjected to further dewatering, as described above.

The consistency is higher after dewatering than prior to dewatering. The consistency can be readily selected by those of skill in the art. For example, the desired consistency will often be high enough to generate the desired results in pretreatment and hydrolysis, but not so high as to create an at least partially dewatered feedstock that cannot be heated uniformly in the pretreatment reactor. The at least partially dewatered feedstock may have an undissolved solids content in the range of about 18 wt % to about 40 wt %, in the range of about 20 wt % to about 35 wt %, in the range of about 22 wt % to about 32 wt %, or any value therebetween.

Heating

The feedstock may be heated during and/or prior to pretreatment. Without being limiting, the at least partially dewatered feedstock may be heated with steam. This may involve utilizing commercially available mixing devices designed for introducing steam and optionally sulfurous acid and/or sulfur dioxide. The acid may be introduced through one or more spray nozzles.

The at least partially dewatered lignocellulosic feedstock is optionally fed to a heating device, such as a heating chamber, in which the feedstock is treated with at least steam. Without being limiting, the feedstock may be broken up as it is conveyed through the heating chamber. The heating chamber may be a horizontally-oriented or essentially horizontally-oriented device. The feedstock may be heated by direct steam contact, which allows for efficient heat transfer.

The at least partially dewatered feedstock need not be fed directly into a heating device. Any of a variety of known devices may be positioned between a dewatering device and the heating device. Without being limiting, examples of such devices include mechanical restricting devices, restraining devices, scrapers and conveyors. It should be understood that the plug may break into segments as it is discharged from the plug formation device, or into other devices positioned downstream of the plug formation device, or as it is fed into the heating chamber.

Pretreatment

In general, pretreatment refers to one or more steps wherein the lignocellulosic biomass is treated in order to make the cellulose in the lignocellulosic biomass more susceptible and/or accessible to enzymes in a subsequent hydrolysis. For example, in one embodiment, the lignocellulosic feedstock and an acid (i.e., sulfur dioxide, sulfurous acid, or a combination thereof) are fed into a pretreatment reactor, wherein they reside for a predetermined time. The acid and feedstock may be added to the pretreatment reactor separately or together. For example, as mentioned, the sulfur dioxide and/or sulfurous acid may be introduced to the lignocellulosic feedstock upstream of the pretreatment reactor or in the pretreatment reactor. For example, in one embodiment, the sulfur dioxide and/or sulfurous acid is introduced during soaking or upstream of soaking. In one embodiment, the sulfur dioxide and/or sulfurous acid is introduced during and/or after dewatering. In another embodiment, the lignocellulosic feedstock is heated prior to entering the pretreatment reactor and/or while in the pretreatment reactor. In one embodiment, the sulfur dioxide and/or sulfurous acid is introduced directly into a heating device or mixer prior to the pretreatment reactor. In one embodiment, the heating includes direct steam injection. In one embodiment, the sulfur dioxide and/or sulfurous acid is introduced directly into the pretreatment reactor (e.g., before and/or during heating).

In one embodiment, the feedstock is contacted with sulfur dioxide gas and/or an aqueous solution comprising sulfurous acid. Sulfurous acid is produced upon the addition of sulfur dioxide to an aqueous solution. As described previously, the feedstock may be soaked in an aqueous solution comprising sulfurous acid and subsequently subjected to elevated temperature to pretreat the feedstock or soaking can be conducted with water and the acid can be added downstream of soaking, but prior to or during pretreating.

Optionally, the pretreatment additionally comprises contacting the feedstock with other acids or chemicals besides sulfurous acid and/or sulfur dioxide. For example, sulfur dioxide and/or sulfurous acid can be added to the feedstock during soaking or upstream of soaking. During or after soaking, sulfuric acid may be added to the dewatered feedstock. Addition of the acids in this manner can improve the economics of the process. In another example, the pretreatment may also be conducted in the presence of up to 50 g/L ethanol that is recycled from downstream in the process, for example so as to reduce the energy usage in the process.

The pretreatment may be conducted so as to disrupt the fiber structure of the lignocellulosic feedstock and increase its surface area to make it more susceptible to hydrolysis by cellulase enzymes. The pretreatment may be performed so that a certain degree of xylan hydrolysis is achieved and only a small amount of conversion of cellulose to glucose occurs. The pretreatment may be conducted by lowering the pH and increasing the temperature of the lignocellulosic feedstock.

The pretreatment may be conducted to achieve a pH in the range of about 1.0 to about 3.0 or in the range of about 1.0 to about 2.5. The pH is measured by taking a sample of a feedstock composition after the addition of acid is complete, and measuring the pH at ambient temperature. If the acid is added prior to pretreatment, the pH is measured on a sample prior to pretreatment. When acid is added during pretreatment, the pH is measured on a sample after pretreatment.

In one embodiment, the pretreatment includes heating the lignocellulosic to a predetermined temperature or temperature range. For example, without being limiting, the maximum temperature may be in the range of about 120° C. to about 230° C., or in the range of about 150° C. to about 230° C. In practice, there may be a time delay in the pretreatment process before the feedstock reaches the maximum temperature. The time that the feedstock is held at this temperature may be dependent on the feedstock and/or any pretreatment chemicals that are present. For example, in one embodiment, the feedstock will be held at the maximum temperature for a duration in the range of about 10 seconds to about 30 minutes. After the pretreatment time has elapsed, the pretreated material may be discharged from the pretreatment reactor. In one embodiment, the pressure is reduced to atmospheric using one or more flash tanks. Once the pressure has been lowered (e.g., to atmospheric) and the feedstock cooled (e.g., to about 100° C. or below), the pretreated feedstock composition may be fed to hydrolysis. One example of a suitable pretreatment system is disclosed in WO 2010/022511.

In another embodiment, the pretreatment may be carried out at a maximum temperature that is between 150° C. and 190° C. Under such pretreatment conditions, fewer and/or lower concentrations of inhibitors may be produced. This is advantageous in that the enzymatic hydrolysis performance may be improved, thereby reducing enzyme usage. Under such temperature conditions, less than 2.5% weight of furfural relative to the weight of feedstock may be produced. For example, in one embodiment, less than 1.75 g/L of furfural is produced. In another embodiment, less than 1.5 g/L of furfural is produced.

The pretreated feedstock composition will comprise dissolved solids. The dissolved solids are measured as set forth in Example 2. Generally, the measurement methodology involves filtering the pretreated feedstock composition, collecting the filtrate and drying the filtrate. Examples of dissolved solids include xylose, glucose, and arabinose sugar, organic acids including acetic acid and glucuronic acid, lignin and soluble products of reactions between sulfurous acid and lignin, such as sulfonic acids and lignosulfonic acids, soluble sugar degradation products and/or one or more salts, such as sulfite salts. The soluble degradation products also include inhibitors, which are described in more detail below. Some examples of a soluble sugar degradation products include furfural, which may be derived from C5 sugars, and hydroxymethylfurfural (HMF), which may be derived from C6 sugars. In general, the pretreatment (e.g., catalyzed by sulfur dioxide and/or sulfurous acid) may solubilize a relatively large portion of the lignin. For example, in one embodiment, up to 30% of the lignin may be dissolved.

As set forth above, according to one embodiment, the pretreated feedstock composition is fed to an enzymatic hydrolysis with little or no washing or other processing that removes a significant amount of dissolved solids (e.g., such as lime precipitation). For example, in one embodiment the pretreated feedstock composition is fed to enzymatic hydrolysis such that most of dissolved solids are transferred to enzymatic hydrolysis with most of the undissolved solids. In one embodiment, the concentration of dissolved solids fed to the enzymatic hydrolysis is least 30% of the concentration of dissolved solids in the pretreated feedstock composition, measured by weight. The dissolved solids fed to enzymatic hydrolysis may be measured at an inlet to the enzymatic hydrolysis, which is an inlet to a hydrolysis reactor. In one embodiment, the concentration of dissolved solids fed to the enzymatic hydrolysis is at least 50% of the concentration of dissolved solids in the pretreated feedstock composition. In one embodiment, at least 55% (w/w), at least 60% (w/w), at least 65% (w/w), at least 70% (w/w), at least 75% (w/w), at least 80% (w/w), at least 85% (w/w) or at least 90% (w/w) of the dissolved solids in the pretreated feedstock composition are fed to the enzymatic hydrolysis. Providing little or no washing of the pretreated feedstock composition is advantageous in that it requires less process water and provides a simpler process. Moreover, providing little or no washing allows at least some inhibitors produced in pretreatment to be carried over to the enzymatic hydrolysis, and thus may provide some anti-microbial effects. However, since the process uses sulfur dioxide and/or sulfurous acid, less potent soluble sugar degradation product(s) may be produced (e.g., relative to pretreatments using sulfuric acid as the only acid).

In one embodiment, the sulfur dioxide and/or sulfurous acid pretreatment is followed by an enzymatic hydrolysis that is conducted at a temperature above about 58° C. Accordingly, the presence of some inhibitors (e.g., even if at a low potency) and the increased temperature may reduce the risk of microbial contamination to the point that the overall amount of enzyme may be reduced even though the pretreated feedstock is not substantially washed, diluted, or processed. Advantageously, conducting the hydrolysis at a temperature above about 58° C., and in particular at a temperature above about 62.5° C., may reduce the amount of water used to address the slow temperature rise of the slurry during hydrolysis. Accordingly, the resulting process, which also provides little to no washing of the pretreated material, reduces the amount of cooling water needed.

In one embodiment, there is little washing, dilution, or processing of the pretreated feedstock composition prior to the enzymatic hydrolysis. In one embodiment, there is no washing of the pretreated feedstock composition prior to enzymatic hydrolysis. According to another embodiment, less than 10% (w/w) of the aqueous phase of the pretreated feedstock composition is removed prior to hydrolysis or less than 20% (w/w) is removed prior to hydrolysis.

According to one embodiment, at least 50% (w/w) of the amount of furfural in the pretreated feedstock composition is retained and fed to the enzymatic hydrolysis. According to another embodiment, at least 60% (w/w) of the amount of furfural in the pretreated feedstock composition is retained and fed to the enzymatic hydrolysis. According to another embodiment, at least 70% (w/w) of the amount of furfural in the pretreated feedstock composition is retained and fed to the enzymatic hydrolysis. According to another embodiment, at least 80% (w/w) of the amount of furfural in the pretreated feedstock composition is retained and fed to the enzymatic hydrolysis. The amount of furfural may be measured by HPLC.

According to one embodiment, at least 50% (w/w) of the amount of xylose in the pretreated feedstock composition is retained and fed to the enzymatic hydrolysis. According to another embodiment, at least 60% (w/w) of the amount of xylose in the pretreated feedstock composition is retained and fed to the enzymatic hydrolysis. According to another embodiment, at least 70% (w/w) of the amount of xylose in the pretreated feedstock composition is retained and fed to the enzymatic hydrolysis. According to another embodiment, at least 80% (w/w) of the amount of xylose in the pretreated feedstock composition is retained and fed to the enzymatic hydrolysis. The amount of xylose may be determined using HPLC.

According to a further embodiment, the process steps carried out between pretreating and enzymatic hydrolysis may "consist essentially of" cooling and adjusting the pH of the pretreated feedstock composition. By this it is meant that additional steps may be included between pretreating and hydrolysis of cellulose with cellulase enzymes besides cooling and pH adjustment that do not materially increase water usage in the process. Without being limiting, this may include steps such as centrifuging and/or pressing of the pretreated feedstock composition. A pressing of the solids or a small amount of washing and/or dilution may be conducted, consistent with maintaining greater than 50% concentration of dissolved solids, or greater than 70%, but not necessarily 100% concentration of dissolved solids. Examples of cooling include exposing the pretreated feedstock composition to one or more flashing stages and/or heat exchangers to cool it from the final pretreatment temperature to the temperature at which enzymatic hydrolysis is carried out.

In addition to dissolved solids, the pretreated feedstock composition may include insoluble solids such as cellulose and lignin. The lignin may comprise native and/or sulfonated lignin.

The pretreated feedstock composition is subsequently fed to enzymatic hydrolysis with cellulase enzymes in order to convert the cellulose to glucose. The enzymatic hydrolysis of cellulose using cellulase enzymes is described in more detail below.

Inhibitors

As set forth previously, pretreatment with sulfur dioxide and/or sulfurous acid may generate lower potency inhibitors than other pretreatments such as pretreatment with sulfuric acid.

Inhibitors generated during pretreatment include low molecular weight soluble compounds derived from lignin (e.g., phenolic and non-phenolic compounds), furans such as furfural and hydroxymethylfurfural (HMF), and organic acids such as acetic acid, glucuronic acid, formic acid, levulinic acid and cinnamic acid. For example, some non-limiting examples of inhibitors that may be present in the pretreated feedstock composition include one or more of 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxy methylfurfural, 5-hydroxy methylfurfural, formic acid, acetic acid, levulinic acid, cinnamic acid, coniferyl aldehyde, isoeugenol, hydroquinone, eugenol or combinations thereof.

Furfural, which may be produced during pretreatment with sulfur dioxide and/or sulfurous acid, is an example of an inhibitor that may be used as a measure of the severity of the pretreatment. Furfural is a degradation product of xylose that is often liberated from the xylan components of the lignocellulosic feedstock. In one embodiment, the pretreatment conditions are selected to provide a furfural concentration that is less than 2.5 g/L. In one embodiment, the pretreatment conditions are selected to provide a furfural concentration that is less than 1.5 g/L. For example, selecting the pretreatment chemical to include sulfur dioxide and/or sulfurous acid, using pretreatment reaction times that are less than about 10 min, and/or using pretreatment temperatures that are lower than about 210° C. are some approaches to lowering the furfural concentration at the end of pretreatment. For example, in one embodiment, pretreatment includes introducing sulfur dioxide into a lignocellulosic feedstock containing pretreatment reactor (e.g., between 1 and 30% (w/w dry substrate) for less than 10 minutes at about 190° C. The concentration of furfural may be determined by HPLC.

Another inhibitor often present in a pretreated feedstock composition is acetic acid. Acetic acid arises from acetyl groups present on the lignocellulosic feedstock. The acetyl group is present as a side-chain substituent on xylan with the chemical formula C(O)CH, and may be linked to a beta-1,4 linked xylan backbone polymer of the hemicellulose. As would be appreciated by those of skill in the art, the position and frequency of substitution of the acetyl group side chains attached to xylan varies among feedstocks.

As is known to those of skill in the art, the particular species of this organic acid present in solution depends on the pH. As the pKa of acetic acid is about 4.75, acetate species will be more predominant above the pH corresponding to the pKa, and below this pH, acetic acid will be more predominant. For example, at pH 4.0, about 14.8 mole % of the acid is present as acetate. Thus, the use of the term "acetic acid" does not connote that the protonated species is predominant and the use of this term encompasses acetic acid, acetate, or a combination of these species.

The concentration of acetic acid in the pretreated feedstock composition may be less than about 5 g/L. For example, the acetic acid may be present in the pretreated feedstock composition at a concentration of between 0.01 to 5.0 g/L, 0.25 to 10.0 g/L or 0.5 to 5 g/L. The concentration of acetic acid, acetate, or a combination thereof, is measured using known techniques as disclosed in US 2012/0231514, which is incorporated herein by reference and particularly for the purpose of describing measurements using such known techniques.

In general, the presence of sugar degradation products, such as furfural, hydroxymethylfurfural and acetic acid, produced during pretreatment is believed to reduce the performance of enzymes and/or yeasts used in the enzymatic hydrolysis and/or fermentation, respectively. Accordingly, it is common to reduce the inhibition effects by washing and/or diluting the pretreated feedstock, thus reducing the concentration of inhibitors.

As discussed previously, fewer and/or lower concentrations of inhibitors are present after pretreatment with sulfur dioxide and/or sulfurous acid compared to other pretreatment methods, such as sulfuric acid pretreatment, which may improve enzyme efficiency (e.g., permitting reduced enzyme usage). On the other hand, the lower potency of inhibitors, or other factors arising from the use of sulfur dioxide and/or sulfurous acid, may increase the likelihood of bacterial contamination. However, by conducting the hydrolysis at a temperature selected to reduce microbial growth (e.g., a temperature greater than 60° C.) or to destroy a portion of the microbes (e.g., a temperature greater than about 62.5° C.), the likelihood of contamination being a significant problem may be reduced. Advantageously, this reduction in bacterial contamination, may contribute to a similar amount of ethanol being produced with a reduced amount of enzyme (e.g., relative to a sulfuric acid pretreatment wherein the pretreated feedstock is washed). Further advantageously, this enzyme reduction may be achieved without using sterile or aseptic conditions. Notably, microbial contamination may be a serious concern in pilot and/or commercial systems, wherein the entire system may need to be shut down.

Enzymatic Hydrolysis

The temperature of the pretreated feedstock composition may be adjusted so that it is within the optimum range for the activity of the cellulase enzymes and to prevent, reduce or eliminate microbial contamination. As discussed below, a suitable temperature can be selected based on the temperature optimum for a cellulase enzyme or mixture thereof.

As would be appreciated by those of skill in the art, since pretreatment is conducted at elevated temperature, typically between about 150° C. and about 230° C., the temperature of the pretreated feedstock composition may be cooled to achieve a temperature compatible with the enzyme used. Examples of cooling include exposing the pretreated feedstock composition to one or more flashing stages and/or heat exchangers to cool it from the final pretreatment temperature to the temperature at which enzymatic hydrolysis is carried out.

Examples of suitable temperatures for conducting the enzymatic hydrolysis include temperatures within the following ranges: about 58° C. to about 90° C., or about 60° C. to about 90° C., or about 60° C. to about 80° C., or about 60° C. to about 70° C., or about 60° C. to about 65° C. Further examples of suitable temperatures for conducting the enzymatic hydrolysis include temperatures within the following ranges: about 62.5° C. to about 90° C. or about 62.5° C. to about 80° C. or about 62.5° C. to about 70° C. or about 62.5° C. to about 65° C. Other examples of suitable temperatures for conducting the enzymatic hydrolysis include temperatures within the following ranges: about 65° C. to about 90° C. or about 65° C. to about 80° C. or about 65° C. to about 70° C. or about 65° C. to about 67.5° C. In one embodiment, wherein the risk of microbial contamination may be significantly reduced, the enzymatic hydrolysis is conducted at about 65° C. In addition to cooling, the pH of the acidic pretreated feedstock composition is typically adjusted to a pH at which enzymatic hydrolysis can be conducted. This is a pH value that is suitable for the enzymatic hydrolysis reaction. The pH may be adjusted to between 4 and 7 or more typically between about 4 and about 7.5 or between about 4 and about 7.0, or between about 4 and about 6.5 or between about 4 and about 6. According to further embodiments, the pH is adjusted so that it is less than 8 and is at a value that is compatible with cellulase enzymes. The pH at which a cellulase enzyme is compatible depends on the particular enzyme utilized in the cellulose hydrolysis, but can be determined readily by those of skill in the art.

The pH adjustment may be carried out with an inorganic alkali. The term denotes that both the cation and anion in the alkali compound are inorganic. Any suitable inorganic alkali, or mixtures thereof, can be utilized. Non-limiting examples are the cations, potassium, sodium, ammonium and calcium, and the anions, carbonate and hydroxyl. Ammonia gas is also a suitable inorganic alkali. Preferably, the inorganic alkali may be a carbonate salt. Examples of suitable carbonate salts include calcium carbonate, potassium carbonate or mixtures thereof.

An inorganic alkali can be added to the pretreated feedstock composition after it is cooled, before cooling, or at points both before and after cooling. The point of alkali addition can coincide with the cellulase enzyme addition, or the addition point can be upstream or downstream of the location of the enzyme addition. If the enzyme is added upstream of the alkali addition point, the contact time of the enzyme at the lower pH of the pretreated feedstock composition would typically be minimized to avoid enzyme inactivation. The alkali may be added prior to enzyme addition or simultaneously therewith.

After cooling and pH adjustment, the enzyme may be added to the pretreated feedstock by known techniques. In one non-limiting example, enzyme addition is carried out by adding the enzyme to a reservoir, such as a tank, to form an enzyme solution, which is then introduced to the pretreated feedstock composition. In a further non-limiting example, the enzyme is introduced to the pretreated feedstock composition via chemical injection quills, which are commercially available. Alternatively, enzyme may be injected into the pretreated feedstock composition through appropriately sized tubing or via a pipe.

An appropriate cellulase dosage can be about 2 mg to about 20 mg protein per gram cellulose, or any amount therebetween. In general, the protein may be quantified using either the bicinchoninic acid (BCA) assay or the Bradford assay. Notably, the combination of using pretreatment conditions (e.g., use of sulfur dioxide and/or sulfurous acid) to provide a furfural concentration less than about 2.5 g/L and an enzymatic hydrolysis temperature of at least 58° C., when the pretreated feedstock is not substantially washed or diluted, may reduce enzyme dosage by about 4 fold relative to a sulfuric acid pretreatment. In another embodiment the enzyme dosage may be reduced by at least about 2 fold relative to sulfuric acid pretreatment.

As would be appreciated by those of skill in the art, to compensate for reduced performance, cellulase enzyme dose is often increased when the enzyme is used outside its optimal temperature range. The process disclosed herein may not require such increased enzyme dose or a lower than conventional amount of enzyme can be added to the hydrolysis. Thus, according to certain embodiments, the enzyme dose may be less than 20 mg protein per gram of cellulose or less than 15 mg protein per gram of cellulose.

The pretreated feedstock subjected to enzymatic hydrolysis may have an undissolved solids content in the range of about 10 wt % to about 40 wt %, in the range of about 12 wt % to about 35 wt %, in the range of about 15 wt % to about 30 wt %, or any value therebetween.

The pretreated lignocellulosic feedstock composition may be fed to one or more unmixed hydrolysis reactors, mixed hydrolysis reactor or a combination thereof. The reactors may be operated in batch, continuous, fed-batch modes, or a combination thereof.

Mixing in the mixed hydrolysis reactor(s) may be achieved by any conventional means, including mechanical mixers such as top-mounted, side-mounted, or bottom-mounted impellers, agitators or eductors; rapid movement of liquid slurry streams pumped into or through the vessel; and/or introducing or generating gases or vapours in the vessel. A particularly suitable mixed hydrolysis reactor is a continuous stirred-tank reactor (CSTR reactor).

When the hydrolysis is carried out in a mixed hydrolysis system that includes multiple mixed hydrolysis reactors, the number of mixed hydrolysis reactors in the system depends on the cost of the reactors, the volume of the aqueous slurry, and other factors. For a commercial-scale plant, the typical number of hydrolysis reactors may be, for example, 3 to 12. Preferably, the mixed enzymatic hydrolysis is a continuous process, with continuous feeding of pretreated cellulosic feedstock and withdrawal of the glucose. However, it should be understood that batch and fed-batch processes, or a combination of these, are also included within the scope of the present invention.

Other design parameters of the mixed hydrolysis reactor(s) may be adjusted as required. For example, the volume of a mixed hydrolysis reactor in a cellulase hydrolysis system can range from about 100,000 L to about 20,000,000 L, or any volume therebetween, for example, between 200,000 and 5,000,000 L, or any amount therebetween. The total residence time of the slurry in a hydrolysis system may be between about 12 hours to about 300 hours, or any amount therebetween.

The enzymatic hydrolysis may be carried out in one or more unmixed hydrolysis reactors. By the term "unmixed hydrolysis reactor", it is meant a reactor suitable for conducting an enzymatic hydrolysis with cellulase enzymes therein that does not carry out any active mixing of its contents as is typically employed in mixed hydrolysis reactors. Although the unmixed reactor may operate with a certain amount of localized mixing due to the introduction and withdrawal of liquid and solids from the system, such localized mixing does not result in any significant dispersal or blending of the reactor contents, as would occur in mixed reactors. For example, a small amount of localized mixing may occur at the bottom of an unmixed downflow reactor due to the action of a rotary bottom scraper or other devices employed for removing the reactor contents. Similarly, if the unmixed reactor is an upflow reactor, a small amount of localized mixing may occur at the top of the unmixed reactor due to the withdrawal of the slurry. The power required for the discharge of the slurry is less than 5%, 3% or 1% of the power required to fully mix the slurry using a mixed reactor of conventional hydrofoil impeller design. A suitable height-to-diameter ratio of an unmixed batch or continuous hydrolysis reactor is between about 0.2:1.0 to about 5.0:1.0, or any ratio therebetween.

The number of unmixed hydrolysis reactors in the system depends on the cost of the reactors, the volume of the aqueous slurry, and other factors. For a commercial-scale plant, the typical number of unmixed hydrolysis reactors may be, for example, 1 to 10.

Other design parameters of the unmixed hydrolysis reactor(s) may be adjusted as required. For example, the volume of a unmixed hydrolysis reactor in a cellulase hydrolysis system can range from about 100,000 L to about 30,000,000 L, or any volume therebetween, for example, between 200,000 and 5,000,000 L, or any amount therebetween. The total residence time of the slurry in a hydrolysis system may be between about 12 hours to about 300 hours, or any amount therebetween.

The unmixed and mixed reactors can be in a consecutive or parallel configuration. Those of ordinary skill in the art could readily select a suitable option by weighing the advantages and disadvantages of each design scheme.

According to one particularly advantageous embodiment, the pretreated lignocellulosic feedstock comprising cellulase enzyme is fed to one or more unmixed hydrolysis reactor, as described above, to produce a mixture of partially hydrolyzed cellulose. The mixture of partially hydrolyzed cellulose may subsequently be fed to one or more hydrolysis reactors that hydrolyze the feedstock with mixing, as also described previously. In the one or more unmixed reactor, the enzymatic hydrolysis of the cellulose reduces the viscosity of the pretreated cellulosic feedstock. By reducing the viscosity of the pretreated feedstock using enzymatic hydrolysis, the power requirements associated with mixing are reduced during hydrolysis of the mixture of partially hydrolyzed cellulose in the subsequent mixed hydrolysis reactor(s).

After the enzymatic hydrolysis is complete, the product is glucose and typically any unreacted cellulose. Insoluble solids present in the resulting stream, including lignin, may be removed using conventional solid-liquid separation techniques prior to any further processing. However, it may be desirable in some circumstances to carry forward both the solids and liquids in the sugar stream for further processing. Optionally, additional cellulase enzyme can be added during the time course of the hydrolysis.

Cellulase Enzymes

In one embodiment, the cellulase enzymes include conventional cellulase enzymes having a temperature optimum between about 50° C. and about 55° C. In another embodiment, the cellulase enzyme is an enzyme that exhibits thermophilicity and/or thermostability.

In a general sense, thermophilicity refers to the ability of an enzyme to be active at a temperature that is higher than conventional for cellulases used in industry, such as above 55° C. A "thermophilic cellulase" is a cellulase or mixture of cellulases that has a temperature optimum of at least about 55° C. By the term "temperature optimum", it is meant the temperature at which optimal activity of the particular enzyme or enzyme mixture is observed. The activity of the enzyme or enzymes at different temperatures is measured at a pH at which maximum activity is observed (i.e., optimal pH). The activity of a cellulase enzyme or mixture of cellulase enzymes is assayed at a variety of different temperatures for a known time, and under otherwise identical conditions. The activity is proportional to the rate of conversion of cellulose or other β-glucan to sugar monomers or short oligosaccharides and is determined for each temperature at which the enzyme activity is measured. The substrate used for determination of activity is a cellulose containing substrate corresponding to the pretreated feedstock composition produced by the pretreatment. A plot of relative enzyme activity v. temperature is then prepared and the temperature at which the highest activity is measured is the optimal temperature for the enzyme or enzymes. The method for determining whether an enzyme or enzyme mixture exhibits a temperature optimum greater than 55° C. is set forth in Example 3 below.

The cellulase enzyme mixture may exhibit a temperature optimum in the range of about 55° C. to about 80° C., about 56° C. to about 75° C., about 57° C. to about 75° C., or about 58° C. to about 75° C.

Any of a variety of known thermophilic cellulases may be utilized in the practice of the invention. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI (Cel7a) and CBHII (Cel6a) and at least four EG enzymes, EGI (Cel7B), EGII (Cel5A), EGIII (Cel2A), EGIV (Cel61A), EGV (Cel45A), EGVI (Cel74A), EGII (Cel61B) and EGVIII (Cel5B). As well, EGI, EGII, EGIII, EGV and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12). *Myceliophthora thermophila*, the anamorph of *Thielavia heterothallica*, produces a more complex cellulase enzyme system including at least four cellobiohydrolases (CBH 1a, CBH 1b, CBH2a, and CBH2b), several endoglucanases (including EG1a, EG1b, EG2), several beta-glucosidases, and over twenty proteins belonging to Glycoside Hydrolase (GH) Family 61 (Visser, H., et al., 2011, Industrial Biotech. 7(3): 214-223).

The conversion of cellobiose to glucose is carried out by the enzyme β-glucosidase. Thus, the cellulase enzymes also typically include this enzyme component. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. It is also contemplated that the β-glucosidase enzyme may be modified to include a cellulose binding domain, thereby allowing this enzyme to bind to cellulose.

In addition to CBH, EG and beta-glucosidase, there are several accessory enzymes that aid in the enzymatic digestion of cellulose (see WO 2009/026722 (Scott), which is incorporated herein by reference and Harris et al., 2010, Biochemistry, 49:3305-3316). These include EGIV, also known as glycoside hydrolase 61, swollenin, expansin, lucinen and cellulose-induced protein (Cip). For example, enzymes containing glycoside hydrolase 61 may improve hydrolysis. Glucose can be enzymatically converted to the dimers gentiobiose, sophorose, laminaribiose and others by beta-glucosidase via transglycosylation reactions.

As would be appreciated by those of skill in the art, two generic approaches have generally been taken to obtain cellulase enzymes that are thermophilic. These are (1) screening naturally-occurring cellulase enzymes, such as those produced by thermophiles for optimal activity at a temperature higher than that of cellulase enzymes produced by mesophiles, and (2) using protein engineering to attain thermophilicity. Protein engineering may be employed on enzymes originating from microorganisms that are mesophiles or thermophiles.

The thermophilic cellulase may originate from a fungus or other microorganism that is thermophilic. In one embodiment, the thermophilic cellulase or cellulase enzymes are isolated from extremophiles, originating from severe environments such as extreme heat (such as e.g., hydrothermal vents and natural hot springs). Non-limiting examples of microorganisms that secrete thermophilic and/or thermostable cellulase enzymes are *Thielavia terrestris* and *Myceliophthora thermophila*.

A microorganism that is thermophilic typically exhibits optimum growth at a temperature in the range from about 55° C. to about 90° C. The fungus may be cultivated in a liquid medium containing assimilable carbon and nitrogen sources, and growth promoting co-factors. Expression of the enzymes from the thermophilic microorganism is carried out using known methodology.

The cellulase enzyme or mixture thereof may also be modified to be thermophilic by protein engineering. Such enzymes are described, for example, in U.S. Pat. No. 8,101, 398, in which a proline residue at position 413 of *Trichoderma* cellulase increased its temperature optimum. Such enzymes exhibited a temperature optimum that was increased by 5.6 degrees celsius (see FIG. 6 of U.S. Pat. No. 8,101,398) relative to a parental cellulase. Protein engineering by rational design or site-directed mutagenesis may rely on sequence homology and structural alignment within a family of proteins to identify potentially beneficial mutations using principles of protein stability. Another approach involves directed evolution by construction of a mutant library with selection or screening to identify improved variants and may involve a process of iterative cycles of producing variants with the desired properties. A combination of these strategies may also be employed to produce a thermophilic cellulase.

If a cellulase is derived from an enzyme by a mutation strategy, it may be characterized as having an increase in its temperature optimum relative to a corresponding parent enzyme from which it is derived. For example, the cellulase or a mixture thereof, may exhibit improved thermophilicity with respect to a corresponding parent cellulase if the cellulase exhibits a temperature optimum ($T_{opt}$) that is at least about 1.5° C. greater than the $T_{opt}$ of the parent, or least about 2.0° C. greater, or least about 2.5° C. greater, or least about 3.0° C. greater, or least about 3.5° C. greater, or least about 4.0° C. greater, or least about 3.5° C. greater, or least about 4.0° C. greater, or least about 4.5° C. greater, or least about 5.0° C. greater, or least about 5.5° C. greater, or least about 6.0° C. greater, or least about 4.0° C. greater than the $T_{opt}$ of the parent from which it is derived.

In another embodiment, the cellulase enzyme or enzymes exhibit at least 50% of activity relative to its temperature optimum at the temperature employed during enzymatic hydrolysis. The temperature optimum is measured as set forth in Example 3. For example, the cellulase enzyme or enzymes may exhibit between 50% and 100% of their activity or between 55% and 100% of their activity or between 60% and 100% or between 70% and 100% of their activity at the hydrolysis conditions relative to its temperature optimum.

The cellulase enzyme may also be thermostable. Thermostable cellulase enzymes have also been described and characterized in the literature. For example, variants of *Trichoderma reesei* Cel7A and Cel6A catalytic domains to improve thermostability have been reported (see for example, U.S. Pat. Nos. 7,375,197 and 7,348,168). It has been reported that substitution of the amino acid at the equivalent of position 413 in *T. reesei* Cel6A with a proline in Family 6 cellulases, e.g., a S407P mutation in the *Phanerochaete chrysosporium* Cel6A, confers increased thermostability (WO 2008/025164, St-Pierre et al.).

Enzyme thermostability can be defined by its melting temperature ($T_m$), the half-life ($t_{1/2}$) at a defined temperature, and the temperature at which 50% of the initial enzyme activity is lost after incubation at defined time ($T_{50}$). Determination of enzyme thermostability may be carried out as set forth in U.S. Pat. No. 8,101,398. Thermostable enzymes typically show common structural elements that have been identified as contributing factors to enzyme thermostability when compared to their mesophilic counterparts (e.g. see Sadeghi, M., et al. 2006. Biophys. Chem. 119:256-270). These structural elements include greater hydrophobicity, better packing, increased polar surface area, deletion or shortening of loops, interactions, smaller and less numerous cavities, stability of α-helix, increase in aromatic interactions, additional disulfide bridges or metal binding and glycosylation sites, decreased glycines and enhanced prolines content, increased hydrogen bonding and salt bridges, improved electrostatic interactions, decreased occurance of thermolabile residues, and conformational strain release.

Fermentation

Fermentation of glucose resulting from the enzymatic hydrolysis may produce one or more of the fermentation products selected from an alcohol, a sugar alcohol, an organic acid and a combination thereof.

During fermentation, bacteria can propagate quickly as the optimum conditions of the fermentation are also conducive to their growth. Bacteria can produce unwanted byproducts including lactic acid, acetone and propionic acid. Lactic acid is a common byproduct produced by bacteria such as *Lactobacillus* spp, *Pediococcus* spp, *Leuconostoc* spp and/or *Weissella* spp (among others) during ethanol fermentations. Since the production of such undesirable byproducts decreases the yield of the desired fermentation product (as the bacteria compete with the yeast for fermentable sugars and convert them to undesirable byproducts instead of the fermentation product of interest), by reducing the concentration of unwanted microorganism fed to fermentation by virtue of the high temperature hydrolysis, the product yield during fermentation can be increased. Moreover, reducing the concentration of organic acids and other byproducts produced by unwanted microbes that can be inhibitory to the yeast can further improve the efficiency of the process. The process disclosed herein can also reduce plant shutdown to sterilize equipment, which can translate to a significant increase in revenue from a plant by reducing downtime.

According to certain embodiments of the invention, yeast recycle is employed. Microbial contamination is especially problematic when the concentration of yeast in a fermentor is increased by yeast recycle. Yeast recycle is employed to improve the efficiency of fermentation processes that are subject to slow reaction kinetics relative to glucose such as those involving the conversion of xylose to ethanol or when it is beneficial to increase volumetric conversion rates. Increases in the volumetric rate of conversion of fermentable sugar to ethanol can be achieved by continuously separating yeast from the harvested fermentation broth, such as by centrifugation, and then re-circulating the yeast back to the fermentor. By re-introducing yeast into the reactor in this manner, the concentration of yeast in the fermentor is continuously maintained at a high level, without significant diversion of sugars to cell growth and away from the desired fermentation product. However, as a result of such repeated re-circulation of yeast, unwanted microbes, such as bacteria, are also recycled along with the yeast. As bacteria tend to divide more quickly than yeast, this can lead to significant levels of microbial contamination.

The microbial contaminants may also include contaminating yeast. Examples of contaminating yeast that may potentially be present in the fermentation are species of *Dekkera*, *Candida* and/or *Pichia*.

In one embodiment, the process disclosed herein reduces the concentration of microbial contaminants (in colony forming units per mL of culture or CFU/mL) to about 100-fold less than the concentration of yeast (in colony forming units per mL of culture or CFU/mL). In another embodiment, the process reduces the concentration of microbial contaminants to about $10^3$ CFU/mL or less. For example, conducting the hydrolysis at elevated temperature may reduce the concentration of microbial contaminants in fermentation from greater than about $10^{10}$ to less than about $10^3$ CFU/mL. Bacterial colonies are enumerated via standard plate count methods. Samples may be obtained from a yeast slurry from a yeast recycle step. If yeast recycle is not employed, the sample may be withdrawn from an outlet of a fermentor.

The fermentation may be conducted at a pH between about 4.0 and about 6.0, or between about 4.5 and about 6.0. To attain the foregoing pH range for fermentation, it may be necessary to add alkali to the stream comprising glucose.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (e.g., U.S. Pat. Nos. 5,789,210, 5,866,382, 6,582,944 and 7,527,927 and European Patent No. 450530) or (b) fungal or bacterial xylose isomerase (XI) gene (e.g., U.S. Pat. Nos. 6,475,768 and 7,622,284). Examples of yeasts that have been genetically modified to ferment L-arabinose include, but are not limited to, recombinant *Saccharomyces* strains into which genes from either fungal (e.g., U.S. Pat. No. 7,527,951) or bacterial (e.g., WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation product is recovered, meaning that it is concentrated and/or purified from a fermented solution. A remaining stream contains components besides the fermentation product remaining after the recovery. Non-limiting examples of such components include inorganic salts, unfermented sugars and organic salts.

Recovery of Fermentation Product

If ethanol or butanol is the fermentation product, the recovery is carried out by distillation, typically with further concentration by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is typically operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

A still bottoms stream remaining after ethanol distillation and containing solids is withdrawn from the bottom of one or more of the column(s) of the distillation unit. This stream will comprise inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream".

Figure 1:
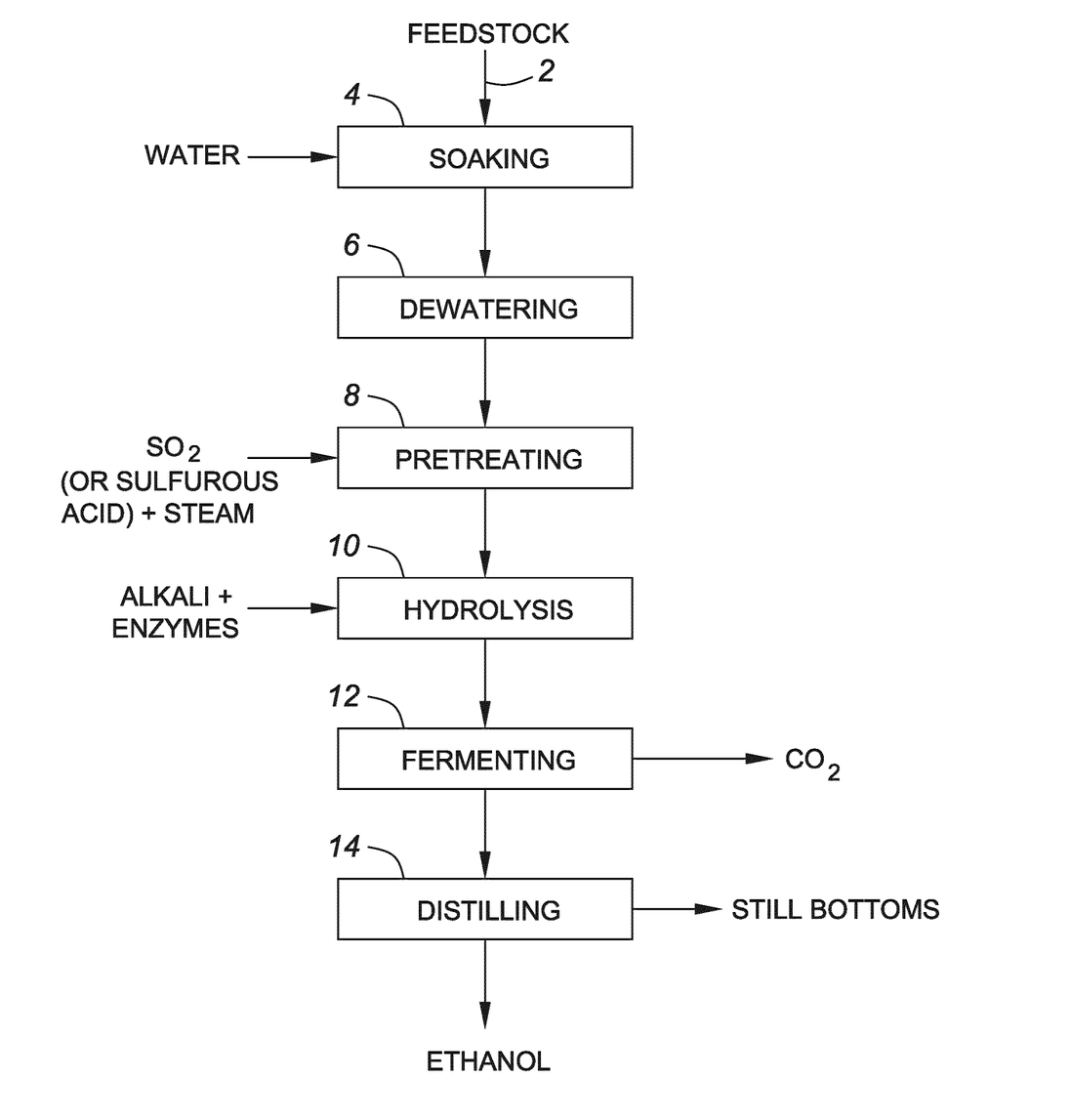
FIG. 1 is a flow diagram of a method according to one embodiment of the invention.

An embodiment of the process disclosed herein is depicted in the flowsheet described in FIG. 1. As shown in FIG. 1, an incoming lignocellulosic feedstock slurry 2 is soaked in an optional soaking step 4, which is water in this embodiment. The soaked lignocellulosic feedstock is optionally dewatered in a dewatering device, such as a screw press, in a dewatering step 6 to produce a partially dewatered lignocellulosic feedstock. The partially dewatered lignocellulosic feedstock is treated with a stream of gaseous sulfur dioxide (e.g., 2% to 30% by weight based on dry weight of feedstock). Upon addition of the stream of gaseous sulfur dioxide to the partially dewatered lignocellulosic feedstock, sulfurous acid may be produced. The acidified feedstock is then fed to a pretreatment reactor where pretreating 8 is conducted at a pH of between 1.0 and 2.5 and a temperature between 160° C. and 230° C. is achieved with steam addition to produce a pretreated feedstock composition comprising sugars selected from xylose, glucose, arabinose, mannose and galactose, soluble products from the reaction of lignin with sulfur dioxide and/or sulfurous acid including sulfonic acids, sulfite salts, sulfonic acid salts, and soluble native lignin, and unhydrolyzed cellulose and insoluble lignin (native and sulfonated).

The pretreated feedstock composition comprising the unhydrolyzed, pretreated feedstock is cooled to 60° C.-90° C. Alkali is added to the pretreated feedstock slurry to achieve a pH between 4 and 7. In this example, the alkali added to adjust the pH of the pretreated feedstock is ammonium hydroxide.

The pretreated feedstock, typically in the form of a slurry, is then subjected directly to enzymatic hydrolysis 10 at a temperature in the range of about 60° C. to about 70° C. in which the cellulose is hydrolyzed to glucose with cellulase enzymes that are thermophilic. The hydrolysis 10 is conducted by adding thermophilic cellulase enzymes at a dosage of 2 mg to 20 mg protein per gram of cellulose for 12 hours to 200 hours. The cellulose hydrolysis 10 produces a hydrolyzate stream comprising glucose. The hydrolyzate stream resulting from the hydrolysis 10 is cooled and fed to a fermenting step 12 to produce ethanol using *Saccharomyces cerevisiae* yeast under conventional conditions.

The hydrolyzate stream fed to the fermenting 12 will contain fewer microbial contaminants than produced in a conventional process due to the relatively high temperature of the hydrolysis. For example, fewer *Lactobacillus* microbial contaminants will be present during the fermentation 12, thereby resulting in less diversion of sugars to lactic acid. During fermentation 12, bacteria can propagate quickly as the optimum conditions of the fermentation are also conducive to their growth. Bacteria can produce unwanted byproducts including lactic acid, acetone and propionic acid. Lactic acid is a common byproduct produced by bacteria such as *Lactobacillus* spp, *Pediococcus* spp, *Leuconostoc* spp and/or *Weissella* spp (among others) during ethanol fermentations. Since the production of such undesirable byproducts decreases the yield of the desired fermentation product (as the bacteria compete with the yeast for fermentable sugars and convert them to undesirable byproducts instead of the fermentation product of interest), by reducing the concentration of unwanted microorganisms fed to fermentation, the product yield during fermentation 12 can be increased. Moreover, reducing the concentration of organic acids and other byproducts produced by microbial contaminants that can be inhibitory to the yeast can further improve the efficiency of the process. The process disclosed herein can also reduce plant shutdown to sterilize equipment, which can translate to a significant increase in revenue from a plant by reducing downtime.

The fermentation 12 produces a fermented slurry comprising the ethanol and carbon dioxide. The fermented slurry is fed to a distilling step 14 in which ethanol is recovered. Distillation 14 produces a concentrated ethanol stream, which may be further concentrated by molecular sieves or other concentration methods. The distillation 14 also produces a product-depleted stream, referred to as a still bottoms stream that remains after distillation 14. The still bottoms remaining after distillation 14 may be processed and/or disposed of.

Examples

Example 1: Determination of Undissolved Solids Concentration

The determination of the undissolved solids (UDS) content is carried out as follows. A fixed amount of a sample containing undissolved solids is dispensed into a plastic weigh dish and the weight is recorded accurately using an analytical scale. A glass microfiber filter paper circle of pore size 1.6 microns, appropriately sized for a Buchner funnel, is placed in an aluminum weighing tin and the combined weight of the tin and filter paper is recorded. After transferring the pre-weighed filter paper to the Buchner funnel, the pre-weighed sample is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care is taken to ensure the solids are quantitatively transferred. After drying the aluminum tin in a 105° C. oven overnight, the contents are weighed accurately and the UDS is quantified by determining, as a percent, the number of grams of dry solids per gram of sample.

Example 2: Measurement of Dissolved Solids Concentration in a Pretreated Feedstock Composition The determination of the dissolved solids concentration of a pretreated feedstock composition is carried out as follows. A glass microfiber filter paper circle of pore size 1.6 microns that has not been pre-wetted is placed in a Buchner funnel. A sample of a pretreated feedstock composition is applied to the filter paper (e.g., 5.5 or 9.0 cm paper depending on size of sample) and filtered by vacuum. The filtrate is collected and weighed into a pre-weighed aluminum tin. After drying the aluminum tin in a 105° C. oven overnight, the contents are weighed accurately using an analytical balance and the dissolved solids are quantified by determining, as a percent, the number of grams of dry solids per gram of filtrate.

The dissolved solids in the pretreated feedstock composition fed to enzymatic hydrolysis and that of the pretreated feedstock composition produced by pretreatment are determined by the foregoing method. A percentage is then calculated from the two values to arrive at a value representing the percent (w/w) of the dissolved solids in the pretreated feedstock composition resulting from pretreating that is fed to the subsequent step of enzymatic hydrolysis.

Example 3: Determination of Cellulase Enzyme Thermophilicity

The thermophilicity of an enzyme or enzyme mixture may be determined by measuring the release of reducing sugar from a soluble β-glucan substrate at different temperatures. Specifically, in a 300 μL PCR plate, 50 μL of enzyme is mixed with 50 μL of pre-heated, pretreated feedstock. The pretreated feedstock is obtained from a pretreatment conducted with sulfur dioxide and/or sulfurous acid as described herein. The pretreated feedstock is adjusted to pH 4.5-5 with 55 mM sodium citrate pH 5.0 in 10 different columns of the PCR plate. Mixtures are incubated for 30 min. at 10 or more different temperatures within a range that is selected based between 55° C. and 70° C. (e.g., 56, 56.5, 57, 57.5, 58, 58.5, 59, 59.5, 60, 60.5, 61, 61.5, 62 and 62.5° C.). Released reducing sugars are then measured by adding 100 μL of a DNS reagent (10 g/L 3,5-Dinitrosalicyclic acid, 10 g/L sodium hydroxide, 2 g/L phenol and 0.5 g/L sodium metabisulfate) to each well, followed by incubation for 20 minutes at 95° C.

Once the temperature decreases below 40° C., 135 μL of each reaction mixture is transferred to individual wells of a 96-well microplate containing 65 μL of Rochelle salts (40% Sodium potassium tartrate) in each well and absorbance at 560 nm is measured using a Fluostar Galaxy microplate reader equipped with a 560 nm filter. The baseline is measured using a no enzyme control, which lacks the enzyme but is the same in other respects. The activity (e.g., measured using released reducing sugar) for each temperature is expressed in percentage relatively to a highest value measured. A graph of relative activity v. temperature is then prepared as described above to determine the temperature optimum.

The present invention has been described with regard to one or more embodiments. However, it will be apparent to persons skilled in the art that a number of variations and modifications can be made without departing from the scope of the invention as defined in the claims.

The invention claimed is:

1. A process for producing a fermentation product from a lignocellulosic feedstock comprising:
    (i) treating the lignocellulosic feedstock in one or more stages, thereby producing a pretreated feedstock composition comprising an aqueous phase and solids, said solids comprising cellulose, said aqueous phase comprising furfural, said treating including combining a pretreatment chemical selected from sulfur dioxide, sulfurous acid, or a combination thereof, with the lignocellulosic feedstock;

(ii) feeding a slurry containing at least a portion of the aqueous phase and solids of the pretreated feedstock composition to an enzymatic hydrolysis and hydrolyzing at least a portion of the cellulose to produce glucose; and (iii) feeding at least the glucose to a fermentation and fermenting the glucose with microorganisms to produce the fermentation product, wherein less than 20% of an aqueous phase of the pretreated feedstock composition is removed prior to the hydrolyzing, wherein the pretreated feedstock composition is not processed by lime precipitation, wherein at least 70% (w/w) of an amount of the furfural in the pretreated feedstock composition is retained and fed to the enzymatic hydrolysis, wherein the slurry has a dissolved solids concentration that is at least about 30% of a dissolved solids concentration of the pretreated feedstock composition, wherein said hydrolyzing is conducted at a temperature greater than about 58° C., so as to reduce or prevent bacterial contamination, and wherein said hydrolyzing is conducted with one or more cellulase enzymes at an enzyme dose that is less than 20 mg protein per gram of cellulose.

2. The process of claim 1 wherein said treating includes adding steam, to the lignocellulosic feedstock.

3. The process of claim 1, wherein said treating comprises:
(a) soaking the lignocellulosic feedstock to produce a soaked feedstock; and
(b) at least partially dewatering the soaked feedstock to produce a feedstock that is at least partially dewatered.

4. The process according to claim 3, wherein at least a portion of the pretreatment chemical is added upstream of a pretreatment reactor, said portion of pretreatment chemical added prior to soaking the lignocellulosic feedstock, during soaking of the lignocellulosic feedstock, after soaking the lignocellulosic feedstock, or a combination thereof.

5. The process of claim 1, wherein the temperature of said hydrolyzing is sufficiently high to reduce or prevent *Lactobacillus* contamination relative to a hydrolysis conducted at 55° C. under otherwise identical conditions.

6. The process according to claim 3, wherein the step of at least partially dewatering the soaked feedstock is conducted with a screw press.

7. The process of claim 1, wherein an inorganic alkali is added to the pretreated feedstock composition subsequent to the treating and prior to hydrolyzing to increase the pH of the pretreated feedstock composition to a pH at which the hydrolyzing is conducted.

8. The process of claim 7, wherein the pH is increased to a value in the range of about 4 to about 7.5.

9. The process of claim 7, wherein the inorganic alkali is calcium carbonate or potassium carbonate.

10. The process according to claim 1, wherein said treating comprises pretreating the lignocellulosic feedstock, said pretreating comprising introducing at least one of the pretreatment chemical and steam into a pretreatment reactor, the pretreatment reactor containing at least a portion of the lignocellulosic feedstock.

11. The process of claim 10, wherein the pretreating is conducted at a temperature in the range of about 170° C. to about 230° C.

12. The process of claim 10, wherein the pretreating is conducted at a pH in the range of about 1.0 to about 2.5.

13. The process of claim 10, wherein the pretreating is conducted for a duration in the range of about 10 seconds to about 30 minutes.

14. The process of claim 1, wherein at least 50% (w/w) of the dissolved solids in the pretreated feedstock composition are retained and fed to the enzymatic hydrolysis.

15. The process of claim 1, wherein at least 70% (w/w) of the of dissolved solids in the pretreated feedstock composition are retained and fed to the enzymatic hydrolysis.

16. The process of claim 3, wherein between the soaking and the hydrolyzing, the undissolved solids content is in the range of about 15 wt % to about 40 wt %.

17. The process of claim 16, wherein between the soaking and the hydrolyzing, the undissolved solids content is in the range of about 15 wt % to about 35 wt %.

18. The process according to claim 10, wherein there is no liquid removal step between the steps of pretreating and hydrolysis.

19. The process of claim 10, wherein there is no solids-liquid separation step between the steps of pretreating and hydrolyzing.

20. The process of claim 10, wherein there is no washing step between the steps of pretreating and hydrolyzing.

21. The process of claim 3, wherein at least a portion of an aqueous solution from the step of soaking is removed during the dewatering and re-used in the process.

22. The process of claim 10, wherein the enzyme used in the enzymatic hydrolysis comprises one or more cellulases.

23. The process of claim 22, wherein the one or more cellulases comprises a thermostable cellulase having a temperature optimum of at least 58° C.

24. The process of claim 22, wherein the one or more cellulases comprises a thermophilic cellulase having a temperature optimum of at least 58° C.

25. The process of claim 1, wherein said hydrolyzing is conducted at a temperature greater than 60° C.

26. The process of claim 1, wherein said hydrolyzin conducted at a temperature greater than 62.5° C.

27. The process of claim 1, wherein said hydrolyzing is conducted at a temperature greater than 65° C.

28. The process of claim 1, wherein said lignocellulosic feedstock is a non-woody lignocellulosic feedstock.

29. The process of claim 25, wherein a concentration of the dissolved solids at an inlet to the enzymatic hydrolysis is greater than about 50% of a concentration of the dissolved solids in the pretreated feedstock composition.

30. The process of claim 1, wherein a concentration of furfural in the pretreated lignocellulosic composition is less than about 1.75 g/L.

31. The process of claim 1, wherein a concentration of furfural in the pretreated lignocellulosic composition is less than about 1.5 g/L.

32. The process according to claim 1, wherein said hydrolyzing comprises adding cellulase having an optimum temperature of at least 50° C. and not more than 55° C.

33. The process according to claim 1, wherein said hydrolyzing comprises adding having the cellulase as an enzyme mixture and wherein the enzyme mixtures has an optimum temperature of at least 58° C. and not more than 75° C.

34. The process according to claim 1, wherein preparing said slurry consists essentially of cooling the pretreated feedstock composition and increasing the pH of the pretreated feedstock composition to a pH of the enzymatic hydrolysis.

35. A process for producing an alcohol from a lignocellulosic feedstock comprising:

(i) soaking the lignocellulosic feedstock in an aqueous solution to produce a soaked feedstock;

(ii) at least partially dewatering the soaked feedstock to produce a feedstock that is at least partially dewatered;

(iii) pretreating the partially dewatered feedstock with heat at a temperature in the range of about 170° C. to about 230° C. to produce a pretreated feedstock composition, wherein sulfur dioxide, sulfurous acid, or a combination thereof, are added: (a) to the aqueous solution used in the soaking, (b) to the lignocellulosic feedstock prior to soaking, (c) to the lignocellulosic feedstock after the step of soaking and prior to or during pretreating, or (d) a combination thereof;

(iv) feeding at least 70% (w/w) of the amount of dissolved solids in the pretreated feedstock composition to an enzymatic hydrolysis, wherein said dissolved solids comprise at least furfural and the dissolved solids concentration is at least about 30% of the dissolved solids concentration of the pretreated feedstock composition;

(v) hydrolyzing the cellulose from the pretreated feedstock composition in the enzymatic hydrolysis to produce glucose, said hydrolyzing conducted with one or more cellulases at an enzyme dose that is less than 20 mg protein per gram of cellulose, wherein the hydrolyzing is conducted at a temperature greater than 58° C. so as to reduce or prevent bacterial contamination, yeast contamination, or a combination thereof, (vi) fermenting the glucose with microorganisms to produce the alcohol; and (vii) recovering the alcohol by distillation or pervaporation wherein less than 20% of an aqueous phase of the pretreated feedstock composition is removed prior to the hydrolyzing, wherein the pretreated feedstock composition is not processed by lime precipitation.

* * * * *

UNITED STATES PATENT AND TRADEMARK OFFICE
CERTIFICATE OF CORRECTION

PATENT NO. : 11,008,598 B2  
APPLICATION NO. : 15/550525  
DATED : May 18, 2021  
INVENTOR(S) : Brian E. Foody et al.

Page 1 of 3

It is certified that error appears in the above-identified patent and that said Letters Patent is hereby corrected as shown below:

On the Title Page

On page 2, in Column 1, item (56), Other Publications, Line 4, delete "Cornparitive" and insert --Comparative--.

On page 2, in Column 1, item (56), Other Publications, Line 11, delete "Biotehncol," and insert --Biotechnol.--.

On page 2, in Column 1, item (56), Other Publications, Line 22, delete "H2504" and insert --H2SO4--.

On page 2, in Column 2, item (56), Other Publications, Line 25, delete "pretreatrnents," and insert --pretreatments,--.

On page 2, in Column 2, item (56), Other Publications, Line 37, delete "pp," and insert --pp.--.

On page 2, in Column 2, item (56), Other Publications, Line 71, delete "App" and insert --Appl--.

On page 3, in Column 1, item (56), Other Publications, Line 10, delete "Bioenerg," and insert --Bioenerg.--.

On page 3, in Column 1, item (56), Other Publications, Line 23, delete "2011;" and insert --2011,--.

On page 3, in Column 1, item (56), Other Publications, Line 28, delete "therrnophila," and insert --thermophila,--.

On page 3, in Column 1, item (56), Other Publications, Line 31, delete "cellulose" and insert --cellulase--.

On page 3, in Column 1, item (56), Other Publications, Line 35, delete "2645-2651," and insert Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,008,598 B2

--2845-2851,--.

On page 3, in Column 1, item (56), Other Publications, Line 66, delete "Stearn" and insert --Steam--.

On page 3, in Column 1, item (56), Other Publications, Line 66, delete "Fir).","  and insert --Fir)",--.

On page 3, in Column 2, item (56), Other Publications, Line 8, delete "al,," and insert --al.,--.

On page 3, in Column 2, item (56), Other Publications, Line 15, delete "64-71;" and insert --64-71,--.

On page 3, in Column 2, item (56), Other Publications, Line 38, delete "1967," and insert --1987,--.

On page 3, in Column 2, item (56), Other Publications, Line 44, delete "Chern." and insert --Chem.--.

On page 3, in Column 2, item (56), Other Publications, Line 45, delete "ai.," and insert --al.,--.

On page 3, in Column 2, item (56), Other Publications, Line 48, delete "F, H.," and insert --F. H.,--.

On page 3, in Column 2, item (56), Other Publications, Line 57, delete "1995." and insert --1995,--.

On page 3, in Column 2, item (56), Other Publications, Line 71, delete "Fractionism" and insert --Fractionation--.

On page 4, in Column 1, item (56), Other Publications, Line 20, delete "Bioresouces," and insert --Bioresources,--.

On page 4, in Column 1, item (56), Other Publications, Line 25, delete "Apita," and insert --Appita,--.

On page 4, in Column 2, item (56), Other Publications, Line 4, delete "arid" and insert --and--.

On page 4, in Column 2, item (56), Other Publications, Line 27, delete "621-831," and insert --821-831,--.

On page 4, in Column 2, item (56), Other Publications, Line 30, delete "LeadingTechnologies," and insert --Leading Technologies,--.

On page 4, in Column 2, item (56), Other Publications, Line 30, delete "Prag.," and insert --Prog.,--.

On page 4, in Column 2, item (56), Other Publications, Line 33, delete "Saccharifcation" and insert --Saccharification--.

In the Specification

In Column 3, Lines 9-10, delete "penicillum," and insert --penicillin,--.

In Column 5, Line 63, delete "sorhum)," and insert --sorghum),--.

CERTIFICATE OF CORRECTION (continued)
U.S. Pat. No. 11,008,598 B2

In Column 12, Line 34, delete "pyrogallollol," and insert --pyrogallol,--.

In Column 12, Line 40, delete "anisol," and insert --anisole,--.

In Column 12, Line 61, delete "(e.g.," and insert --e.g.,--.

In Column 17, Line 38, delete "Myceliopthora," and insert --Myceliophthora,--.

In Column 17, Lines 56-57, delete "(CBH 1a, CBH 1b," and insert --(CBH1a, CBH1b,--.

In Column 19, Line 51, delete "occurance" and insert --occurrence--.

In Column 24, Line 37, delete "Dinitrosalicyclic" and insert --Dinitrosalicylic--.

In Column 24, Lines 38-39, delete "metabisulfate)" and insert --metabisulfite)--.

In Column 24, Line 45, delete "Fluostar" and insert --FLUOstar--.

In the Claims

In Column 25, Line 29, Claim 2, delete "1" and insert --1,--.

In Column 25, Line 30, Claim 2, delete "steam," and insert --steam--.

In Column 26, Line 10, Claim 15, delete "the of" and insert --the--.

In Column 26, Line 39, Claim 26, delete "hydrolyzin" and insert --hydrolyzing is--.

In Column 26, Line 59, Claim 33, after "adding" delete "having".